United States Patent
Shuja

(10) Patent No.: US 9,981,203 B2
(45) Date of Patent: May 29, 2018

(54) RAPID DRYING EXTRACTION TARGETING OIL RESIN PLANT EXTRACTS

(71) Applicant: Ahmed Shuja, San Francisco, CA (US)

(72) Inventor: Ahmed Shuja, San Francisco, CA (US)

( * ) Notice: Subject to any disclaimer, the term of this patent is extended or adjusted under 35 U.S.C. 154(b) by 0 days. days.

(21) Appl. No.: 15/729,497

(22) Filed: Oct. 10, 2017

(65) Prior Publication Data

US 2018/0099236 A1    Apr. 12, 2018

Related U.S. Application Data

(60) Provisional application No. 62/406,902, filed on Oct. 11, 2016.

(51) Int. Cl.
*A61K 36/00* (2006.01)
*B01D 11/02* (2006.01)
*C07D 311/80* (2006.01)
*C07C 37/68* (2006.01)

(52) U.S. Cl.
CPC ...... *B01D 11/0211* (2013.01); *B01D 11/0203* (2013.01); *C07C 37/685* (2013.01); *C07D 311/80* (2013.01); *C07C 2601/16* (2017.05)

(58) Field of Classification Search
CPC ...................................................... A61K 36/00
USPC ......................................................... 424/725
See application file for complete search history.

(56) References Cited

PUBLICATIONS

Teh et al., Food Bioprocess. Technol., 2014, 7, 3064-3076.*

* cited by examiner

*Primary Examiner* — Michael V Meller

(57) ABSTRACT

The present method applies Pulsed electric fields adding additional control variables for the extraction of target organic compounds from plant material. A current method of extraction of target Cannabaceae plants during processing provides methods to accelerate drying and extraction of these oil rich plants where the pre-removal of water is beneficial aiding in decreased process times. The methods include applying electric fields to the plant material to accelerate the dehydration, and the extraction of target organic compounds.

9 Claims, 3 Drawing Sheets

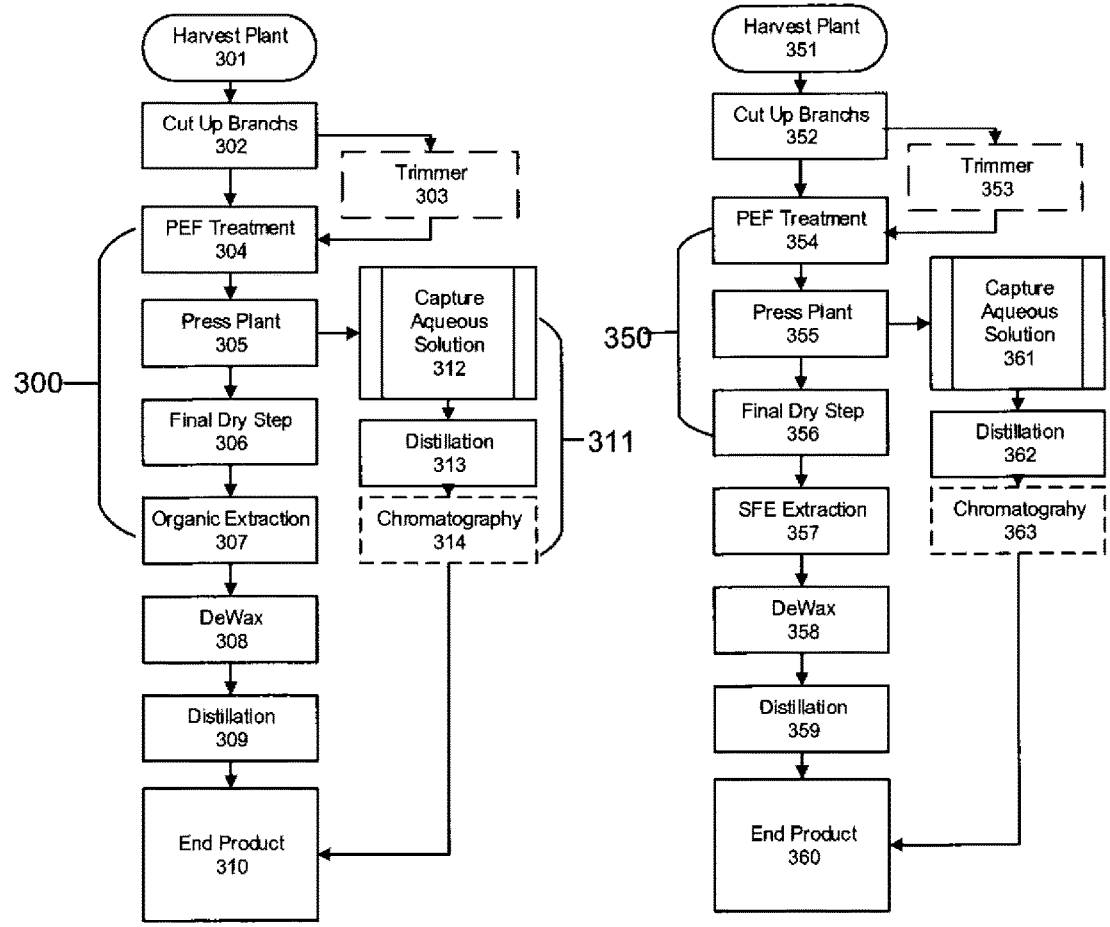
*FIG. 3A*  *FIG. 3B*

RAPID DRYING EXTRACTION TARGETING OIL RESIN PLANT EXTRACTS

CROSS-REFERENCE TO RELATED DOCUMENTS

This application claims priority to U.S. Provisional Patent Application No. 62/406,902 entitled "Pulsed Electric Field Super Critical Extraction", which was filed on Oct. 11, 2016, the contents of which are expressly incorporated by reference herein.

FIELD OF THE INVENTION

The present inventions relates to extraction of lignin rich plants that have oleoresin organic molecules and terpenes that are targeted for human application and consumption.

BACKGROUND

Despite the long history of crops such as hemp, hops and *cannabis* the drying and curing has not changed significantly over the years. Crops such as Hemp and *Cannabis* are grown, feminized and harvested by cutting the plant at the stalk. Hops, or *humulus lupulus* belongs to the family Cannabaceae of which *Cannabis sativa* is also a member. The hop female bears fruit that are important product in beer brewing. These plants are dried to lower the residual water content of less than 10 wt % and ideally around 7 wt % so as to stop the growth of mold and mildew. In the case of Hemp, if the female is allowed to continue to be in the flowering stage before harvest the wt % of Tetrahydrocannabinol (THC) will increase. The production of THC is a result of the female's reproductive cycle. If the concentration THC, a bioactive regulated drug, is allowed to exceed 0.3 wt % regulators will mandate destruction of the crop. The harvest can be limited by the drying of the crop in the case of hemp so either more indoor areas for drying is required or more rapid drying techniques are required.

With these lipid rich crops in recent years a trend has been to extract oil compounds from these plants and use them as flavorings or active drug ingredients. For example, hops is now extracted with super critical extraction from the plant and the oil concentrate is added to beer during fermentation. In recently years the consumption of *cannabis* has been changing to a form of concentrates as opposed to flower that is ignited and smoked. Hemp, as well, is processed by extraction for the purpose of capturing CBD and terpenes for use in medicinal products and health products. There are many methods to carry out extraction of the active compounds that include polar and non-polar solvents.

A popular method of extraction of the active compounds CBD, THC and terpenes is the use of (ETOH) Ethyl Alcohol. This solvent is a readily available polar solvent that can quickly extract target compounds. This solvent is fast but not selective in that it also extracts unwanted compounds such as chlorophyll, wax, lignin and heavy metals. Thus there is a trade off in rapid up front extraction with ETOH with added equipment and labor needed in the post processing.

Super critical fluid extraction (SFE) is a popular technique of extracting non-polar oleoresin based extracts. The carbon dioxide acts as a non-polar solvent and is attracted to non-polar organic molecules such as THC, CBD, fats and lipids. Because the solvent is non polar, selectivity involving the extracts can be created by selection of process parameters such that unwanted chemicals are not extracted such as chlorophyll. Several parameters have an impact on the processing time such as temperature, pressure, solvent flow rate. The equipment used in SFE is more expensive than ETOH extraction equipment due to the need for higher operating pressures.

A recent push in the SFE industry for *cannabis* has been to increase the mass flow rate of the $CO_2$ solvent where equipment manufacturers are moving away from air driven pumps and toward piston driven liquid pumps. The overall push is to minimize the hours per pound that SFE can extract *cannabis*, hemp or hops. This will aid the extraction process during the start-up phase when the solubility limit of the solvent can be reached due to large availability of target organic compounds. After this initial period, the rate limiting step becomes the step involving diffusion of the CO2 solvent into the intracellular material of the plant and the trichome, then back into the mobile solvent phase.

With the above mentioned techniques of processing these oil rich crops, it is common in the industry that daily throughput of *cannabis* extraction be up to 100 lbs/day assuming approximately 30 min/lb for CO2 extraction. This may require some $0.5 million in equipment investment. Additionally it may require a similar investment $0.5 million or double $1.0 million for the drying equipment to speed up drying an curing.

As extraction techniques are scaling up there must be drying techniques that match the production rate of the extraction techniques. Some faster drying equipment is being offered including larger convective ovens, microwave energy, or hot nitrogen blanket drying equipment. By applying thermal or microwave energy to the plant to accelerate drying, heating of the plant matrix will occur. With the additional heating and substrate temperature rise, some of the more volatile terpene compounds may be lost such as mono terpenes and sesquiterpines or other bioactive compounds can be altered. The terpenes themselves, when captured and isolated, can be sold at values nearly equivalent to the targeted oleoresin target compounds such as Tetrahydrocannabinol (THC) and cannabidiol (CBD). Thus it is beneficial to devise a chemical processing scheme that is faster and captures terpenes.

When speeding up the drying and extraction process it would be ideal to overcome two limitations of other techniques. Preservation of thermally liable headspace compounds and the fundamental limitation of diffusion kinetics during extraction. The intent of the inventors work is to create a methodology that minimizes the capital investment in equipment but creates a rapid drying and extraction method in a single production line. The current disclosure reveals methods to increase production through put by several fold with techniques that preserve headspace compounds and reduce diffusion kinetics limitation.

SUMMARY

A recent push in the extraction industry has been to accelerate extraction of key organic compound from plant material primarily by techniques such as super critical fluid extraction or ethanol extraction. These techniques require a drying step to precede the extraction step. This disclosure describes methods to accelerate drying and extraction of oil rich plants where the pre removal of water is beneficial. This invention relates to applying electric fields to plant material to accelerate the dehydration, and the extraction of target organic compounds.

BRIEF DESCRIPTION OF THE DRAWINGS

One or more embodiments of the present invention are illustrated by way of example and are not limited by the FIG. 1 illustrates an super critical fluid extraction curve
FIG. 2 Structure of trichome that produces cannabinoids
FIG. 3A Process description using PEF and pressing scale production using organic solvent for the Cannabaceae family
FIG. 3B Process description using PEF and pressing scale production using SFE extraction for the Cannabaceae family

DETAILED DESCRIPTION

Figure 1:
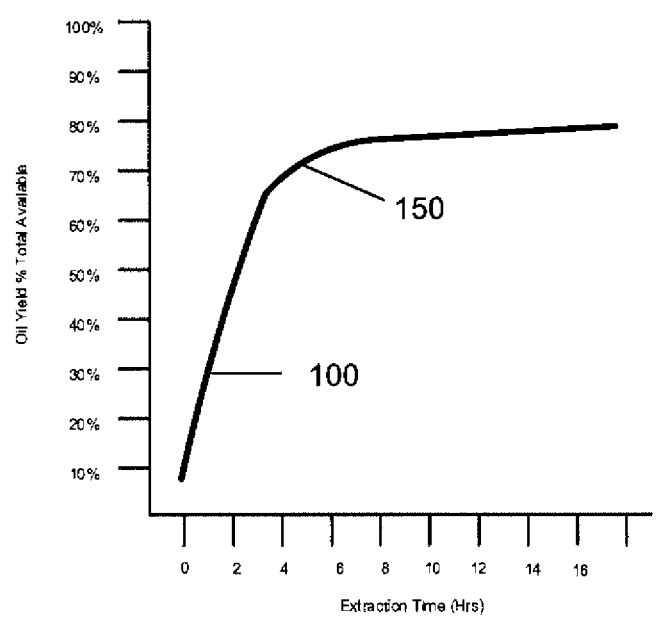

Various aspects of the invention will now be described. The following description provides specific details for a thorough understanding and enabling description of these examples. One skilled in the art will understand, however, that the invention may be practiced without many of these details. Additionally, some well-known structures or functions may not be shown or described in detail, so as to avoid unnecessarily obscuring the relevant description. Although the diagrams depict components as functionally separate, such depiction is merely for illustrative purposes. It will be apparent to those skilled in the art that the components portrayed in this figure may be arbitrarily combined or divided into separate components.

The terminology used in the description presented below is intended to be interpreted in its broadest reasonable manner, even though it is being used in conjunction with a detailed description of certain specific examples of the invention. Certain terms may even be emphasized below; however, any terminology intended to be interpreted in any restricted manner will be overtly and specifically defined as such in this Detailed Description section.

References in this specification to "an embodiment," "one embodiment," or the like mean that the particular feature, structure, or characteristic being described is included in at least one embodiment of the present invention. Occurrences of such phrases in this specification do not necessarily all refer to the same embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The process design of dehydration and extraction of organic compounds from natural products requires an understanding of target plants morphology. A current example of interest is the removal of target cannabinoids from the *cannabis* plant. The *cannabis* plant has cannabinoids in each part of the plant but leaves typically have ~4% where as the buds have 25-30% of target cannabinoids. The organic molecules of interest in *cannabis sativa* include Tetrahydrocannabinol(THC), Delta 9 Tetrahydro-Cannabinol Acid (THCA), Thetrahydrocannabivarin (THCV), Cannabidiol Acid(CBDA) cannabidiol (CBD); cannabiniol (CBN); cannabigerol (CBG); cannabichromene (CBC); cannabidivariol (CBDV); tetrahydrocannabidiol (THCBD); tetrahydracannabidiol (THCBG); tetrahydrocannabichromene (THCBC); tetrahydrocannabidivarol (THCBDV); in total a family of 60 bi- and tri cyclic compounds named cannabinoids collectively referred to as Total Available Cannabinoids (TAC) are heavily concentrated in the trichome.

The FIG. 1. prior art shows a typical extraction curve for SFE. A linear regions 100 will be followed by a folding over in the curve region 150. The liner region 100 is due to the target analyte compound desorbing from the surface of the plant material that has been dried and ground up. The knee in the extraction curve 150 is due to a diffusion limitation where the solvent must diffuse into the cellular matrix of the plant or into the waxy outer layer of the trichome and then dissolve the compound of interest. This diffusion limitation is the rate limiting step in extraction and determines the production throughput for SFE extraction equipment weather it is polar solvent based or non polar solvent based. This feature will be seen if ethonal, butane, propane, chlorofloural carbon, methonal or other polar solvents are used. It will also be seen if non polar solvents are used such as super critical carbon dioxide or subcritical carboxide is used.

Figure 2:
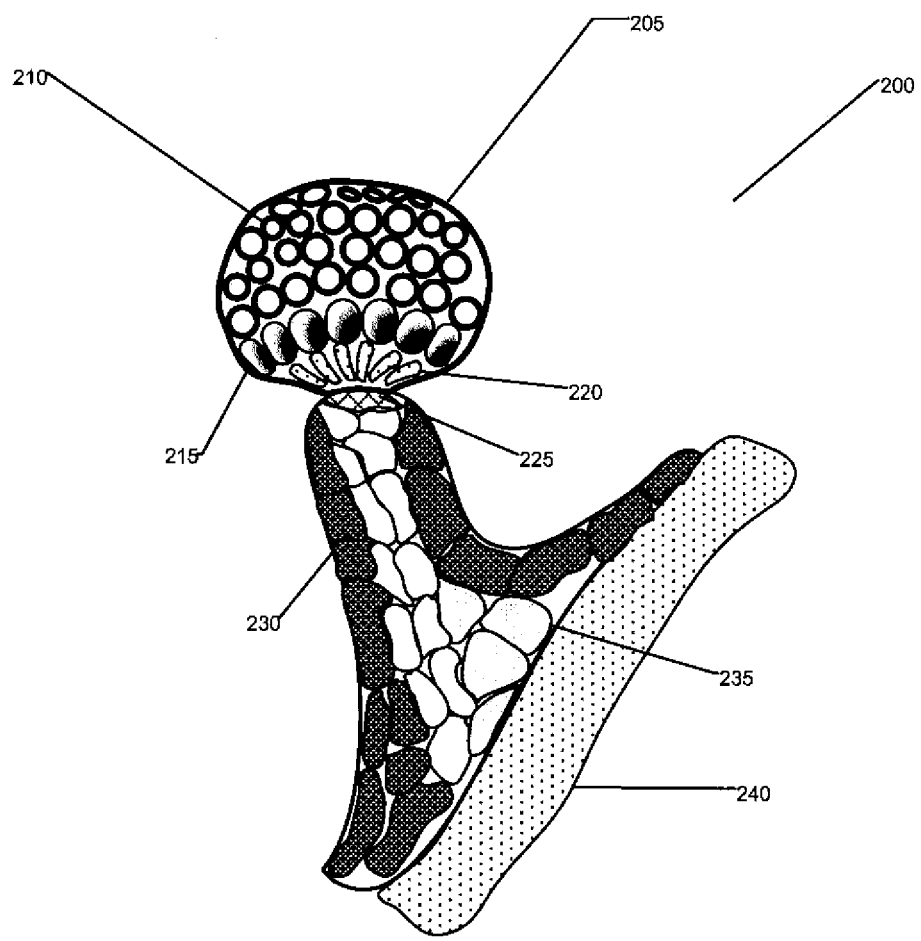

The illustration in FIG. 2 prior art shows the structure of the tricome 200 on the bract 240 of the *cannabis* plant. The trichome is small at 50-100 microns in size. The head of the trichome is round and covered in a cuticle 205 which thickens as flowering progresses. The gland head has stripe cells 210 which churns out its resins and the resin gets deposited in close proximity to the cuticle 205. The secretory cells 215 take nutrients from the phloem and turn them into precursors for cannabinoid and terpenoid metabolism. The basil cell 225 provides the support structure for the gland head. The cuticle, thickens getting richer and richer in oil as flowering progresses. Below the gland head is a structure consisting of epidermal cells 230 and hypodermal cells 235. The hypodermal cells constantly transport nutrients to the gland head. The epidermal cells 230 hold up the gland head and form an outer structure that is connected to the bract 240 of the plant stem. To accelerate the extraction of the target compounds cannabinoids and terpenes it is necessary to disrupt the surface of the cuticle 205 and the cell wall structure of the secretory cell 215. The authors experimental work has shown that by combining PEF and pressing the trichome structure can be opened without significant loss in total available cannabinoid content.

In order to understand the scale of the target compounds to be removed a measure of molecular polar surface can be used. This is a common term used for understanding the molecular compound transport properties through cellular pores and nano-pores created with PEF and is defined as the sum of the surfaces of polar atoms, for example. Oxygen, Hydrogen, Nitrogens in a molecule. In the current example CBD has a topological polar surface area of 40.5 $A^2$ and D9THC, THC is 29.5 $A^2$. The polar surface area of water is 1 $A^2$ i.e. on the order of 30-40× smaller than the primary target compounds. The size difference makes it possible with pulsed electric fields to create openings small enough for water molecules to escape but not large enough for the larger organic molecule. This allows the quick removal of water by differences in osmotic pressure or low power application of thermal, electromagnetic, angular acceleration, or compressive pressure.

Pulsed Electric Field (PEF) is a short intense electric pulse that modifies the cell membrane within a nano- to millisecond, that can allow the ease of migration/diffusion intracellular molecules into an external solvent. The plant material target is placed between at least two electrodes and a power supply is used to generate an electric field. Electroporation of the cell membrane can be tuned by electric field strength, pulse duration, amplitude, repetition frequency, and pulse number). Through parametric exploration electroporation can create opening of different size in the cell membrane to allow the release of molecules based on atomic radius of the molecules. For example a small molecule such as water can be allowed to exit the cellular matrix but large more complex bio active molecules can be too large to escape in the absence of a solvent. add cell disruption via PEF and charge as well as compression, simultaneous, controlling size of nano-pore arber press or other means.

Under the application of PEF an electric field acts to create nano-pores in the cell membrane. By creating pores intercellular diffusion coefficients are increased in the leaves and stems part of the tissue. In the current example where a larger portion of the active compounds may lie below a thick wax cuticle FIG. 2, 205 that can act as a dielectric essentially shielding the internal cells from a combination of PEF with a pressing step is used. In the first step of applying the field treatment in the range of 0.1-12 kJ/kg at 20-30 kV nanopores are formed. Then by application of pressure on the order of two tons or 50-500 BAR the intracellular water is expelled but also the tricome waxy cutter layer is disturbed. This PEF treatment combined with compaction pressure allows for the more rapid and selective removal of the target organic compounds of interest the subsequent extraction step. This means getting rid of the asymptote in the extraction curve 150 of FIG. 1.

A demonstration was completed to illustrate the rapid drying of the *cannabis* plant material as it can be used as a close proxy for hemp, and hops. Typically fresh harvested trim and what remains of the flower is dried by natural convection by laying the material out on plastic tarps for 48 to 60 hours. With the application of PEF at 6 kJ/kg and subsequent pressing at 100 bar and subsequent drying by laying out on a white tarp the plant material was dried in 2 hours. Fluid that was expelled from the plant material was analyzed with gas chromatography and with mass spectrometry and it was found that the THC was present with a concentration of 27.8 ppm 0.0027 wt % of THC the most prevalent cannabinoid. This TAC i.e. cannabinoid content was tested to be present at levels of 7 wt % in the plant tissue in the leaves stems and remnants of flower that constitute what is called trim. The plant material did not experience more than a few degrees increase temperature during the drying process.

In addition, *cannabis* species contain a larger number of related compounds, the terpenes or cannflavins. Often, terpene molecules found in plants produce smell and the Cannabaceae species is especially rich in aromatic terpenes. These compounds can be evaporated during thermal drying, threshing, grinding with the more most common current chemical process to produce tinctures, or perform chemical separation and isolation. Within the context of this disclosure, the term terpene includes Hemiterpenes, Monoterpenes, Polyterpenes, Tetraterpenes, Terpenoid oxides, Sesterterpenes, Sesquiterpenes, and Norisoprenoids. By providing a method to dewater without long periods of hang drying or heated convection these compounds can be captured and concentrated.

In the process example described herein shown in FIG. 3*a* the industrial hemp is harvested 301 and cut down at the stalk but machine driven combine or by hand. The plant material is cut into small pieces 302 with flower and trim together on the order of 12-18" in length. This cutting into smaller pieces can be done by plant sheers or by a pulling the flower and leaves off by hand. Depending on the preferred extraction method an automated trimmer 303 can be used to reduce the cut length of the plant material and separate flower for example a Twister Trimmer which contains cylindrical blades turning in courterclockwise is used for fast plant processing in 303. This green or undried material is exposed to the disclosed fast drying/extraction equipment 300. The first stage is a PEF treatment at step 304 of 0.1-12 kJ/kg at 20-30 kV that can electroporate the plant tissue. Compression is then applied at step 305 to the plant material in the rage of 1-5 tons and the expelled aqueous solution is captured and put into a parallel process at step 312 for subsequent separation and isolation of terpenes. The chromatography process 314 is optional since several resulting products are made with full spectrum terpenes. Continuing along 300 the plant material is conveyed through a final drying step 306 where vacuum drying, microwave energy, centrifugal force, warm air or a combination of which is applied.

The now quick dried material is extracted by way of organic solvent such as ethanol, toluene, fluorocarbon, or aromatic solvent stage 307 where the plant material is exposed to solvent. The organic solvent stage is built into the conveyance of a single line machine. During the extraction organic solvent extraction stage 307 a solvent is pumped into container at room temperature 22 C or in a cooled state as low at −40 C. The solvent is allowed to steep for 1 min to 20 min to remove the target cannabinoids. The selectivity of the solvent can also be tuned by the addition of water as a dilution medium. The solvent in stage 307 is then pumped into a falling film evaporator to separated the extracted oil from the solvent. A falling film system such as one made by Colorado Extracts has the ability to atomize the solvent/extract solution under vacuum and spray along a heated column. This will act to distil out the majority of the solvent and concentrate moves to step 308. The now extracted plant material in 307 is conveyed out to be dried of solvent.

The preceding step is parametrically optimized to reduce the extraction to minutes per batch such that a continuous in line batch process can be completed. The optimization includes residence time in the solvent, solvent dilution with water, temperature adjustment from room temperature to −40 C, active pumping in counter current mode, stationary steeping, circular motion. In the preferred embodiment it includes active belt conveyance, room temperature extraction with 90-100% pure ethanol, low residency time in solvent of 5 minutes or less.

The entire stage of 300 is built into a single conveyor or screw type machine that provides several times the current production rates. Companies that make scewtype conveyers include Kingreat where sludge is dewater from wastewater. These type of machines can be reconfigured to include the PEF. Also more than one stage can be created such that the 304-307 are built into an equipment platform.

The entire stage of 300 can be built on a conveyor type system such as conveyor system made by Jiaozuo Xingram Industrial and Trading Co., Ltd that offer long conveyor belts for the mining or natural extracts products industry. The unit is customized to allow transport from trimmer location into extraction stage 300 where the steps of PEF treatment 304, pressing 305 and final drying 306 and organic extraction 307 happen in discrete stages along the conveyor belt.

Now referring to FIG. 3B, in some embodiments, a supercritical fluid with or without organic solvent modifier such as ethanol may be used as the extractant 357. In FIG. 3b the supercritical fluid extraction is done in a separate step, thus process 350 shows the fast drying 356 with the organic extraction stage 307 removed. Thus 350 contains PEF treatment 354, a pressing stage 355, and a final drying step 356 such that the plant material will leave the rapid drying stage 356 and move into a separate SFE extraction 357 platform that processes large batch volumes i.e. 10's to 100's, 1000's of pounds at a time. Adjustment in temperature and pressure in the extraction and separation can adjust the selectivity of SFE and this can be used to extract specific compounds. The compounds can be separated due to differences in thermophysical properties such as solubility and condensation temperature, and pressure.

With the use of equipment SFE equipment with high mass flow rate for example Q90L by Vitalis with 15 kg/min mass flow rate compared to Waters 2×5 L at 0.3 kg/min the system can be ran at extraction pressures of 1100-2000 psi at lower temperature i.e. 55 C, or between 25-50 C, or ideally 28-35 C. The separation stages can be ran at 850 psi to 1000 psi. Since the mass flow rate is very high in stage 357 and the plant material has undergone stage 350 at very low pressures the target cannabinoids are removed at 5 min/lb to 30 min/lb range. This results in a light yellow extract rich in cannabinoids and low in wax, lipid content that requires much less cuticle wax and lipid removal. Also the capture of the more volatile terpenes is easier under lighter extraction conditions. Typically after the first 1 hr-3 hr of extraction the pressure is increased in the extraction stage to 2000-3500 psi to move into supercritical phase. This switch in to higher pressure is done once the diffusion limitation sets in and the extraction of target compounds has slowed. With the addition of step 350 this requirement to increase to supercritical pressures is delayed thus saving time and this first stage of extraction will be rich in THC and less CBD and processing cost by not having to remove as much cuticle wax and lipids.

The SFE extraction stage can be ran at higher pressures 2000-8000 psi if it is desired to move well into the supercritical phase of $CO_2$. This second step higher pressure step will act to remove any residual cannabinoids and will better target CBD. For example this second step can be run at 1500-2500 psi with the $1^{st}$ separation stage set at 1200 psi and a third set at 850-900 psi. The temperature can be set to 20 C-60 C for this second stage of extraction.

A third example of the SFE stage in 357 can include the extraction chamber being ran in the pressure range of 1200-1500 psi with 10-20 wt % of ETOH as a co-solvent at a temperature of 20-40 C. When combined with the PEF and pressing pre-treatment 350 this will create rapid removal of total available cannabinoids of 1-5 min/lb. The separators of the extraction plant will be set in the range of 860 psi-1000 psi in this use example.

In both FIGS. 3A and 3B the extract will have cuticle wax and lipids. The step of removing non bio active compounds including waxes, fats, lipids, impartial aldehydes, and paraffin is called dewaxing shown as 308 or 358. The raw extract shall be mixed with ethanol at the mixing station using a mechanical overhead stirrer. A ratio of 4:1, 6:1, or 10:1 ethanol to concentrate oil ratio will be used to dissolve the raw extract into solution. The mixture will be covered and placed in the upright freezer until the mixture's temperature reaches −40 C.

In step 308, 358 the chilled mixture is forced though micron filters such as Whatman 100 to 0.3 micron filters to through vacuum assisted bukner funnel to remove plant cuticle wax and lipids. The ethanol oleoresin mixture will be poured into the evaporation flask of the rotary evaporator.

The third step of dewaxing 308, 358 is to place the ethanol-oil mixture into a rotary evaporator under vacuum and low heat, until ethanol precipitation is no longer observed in the collection flask. The rotary evaporator has a large cold trap that will prevent any ethanol vapor from making its way to the vacuum pump or the atmosphere.

When the oil is finished with dewaxing 308, 358 by placing in the rotary evaporator or heated wall falling film distiller. Next the nearly desolvated oil is poured into clean Pyrex or PTFE trays in preparation of vacuum curing to bring the residual solvent to below 500 ppm but ideally to 0 ppm. The vacuum drying also helps remove any remaining water that the rotary evaporator did not remove. The vacuum ovens each have a cold trap placed prior to the vacuum pump in order to ensure that no terpene vapors can escape.

The oil is further concentrated by utilizing distillation techniques 309, 359 such as falling film, wiped film, or spinning band column. The refinement of oil further concentrates the potency of the cannabinoids and separates further plant waxes and lipids.

The water terpene mixture that was collected during rapid drying is further distilled 311 to capture the terpenes captured in the water runoff drying pressing 302. These terpenes and cannabinoids are further refined into isolated compounds utilizing high pressure liquid chromatography 312, for example with reversed phase $C^{18}$ column and a mobile phase made up of for example water, ethonal, methonal, and/or acetonitrile.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed in parallel, or may be performed at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

The invention claimed is:

1. A method of extracting cannabinoids from *cannabis* consisting essentially of the steps of:
   (a) harvesting and cutting live *cannabis*;
   (b) applying a pulsed electric field process to the *cannabis* at a range of 0.1-12 kJ/kg and a voltage of 20,000 volts-30,000 volts which produces the creation of nano-pores on the surfaces of the *cannabis* of a size enabling water to traverse through the nano-pores while retaining desired cannabinoids from the *cannabis*;
   (c) pressing the *cannabis*, simultaneously or consecutively, with a weight, expediting egression of water from the interior of the *cannabis* through the nano-pores;
   (d) drying the *cannabis* to less than 10% wt;
   (e) performing super critical fluid extraction process on the freshly cut *cannabis* using a solvent selected from the group consisting of carbon dioxide, ethanol, cloro-floural carbon, propane and butane, which expedites penetration of the solvent into the freshly cut *cannabis* via the created nano-pores and extracting the desired cannabinoids from the *cannabis*, wherein the size of the nano-pores is controlled by simultaneously applying the kJ/kg and voltage in step (b) and the weight in step (c).

2. The method of claim 1, wherein the pulsed electric field process is conducted with the *cannabis* in an aqueous solution and wherein the aqueous solution serves as a conductor of the kJ/kg and voltage.

3. The method of claim 1, wherein the pulsed electric field process is achieved with the freshly cut *cannabis* cut into lengths forced between compressing rollers and wherein the rollers serve as the conductors of the kJ/kg and voltage.

4. The method of claim 1, wherein the weight is applied in a range of 1-2 tons or pressure at 50-500 bar.

5. The method of claim 1, wherein the selection of the nano-pore size is based on a topological polar surface area of a desired molecule to extract from the *cannabis*.

6. The method of claim 1, wherein a processing time to end of the super critical fluid extraction is decreased compared to extraction processes implemented without the pulsed electric field.

7. The method of claim 1, wherein the cannabinoids are selected from the group consisting of Tetrahydrocannabinol, Delta 9 Tetrahydrocannabinol Acid, Thetrahydrocannabivarin, Cannabidiol Acid, cannabidiol, cannabiniol, cannabigerol, cannabichromene, cannabidivariol, tetrahydrocannabidiol, tetrahydracannabidiol, tetrahydrocannabichromene, tetrahydrocannabidivarol and mixtures thereof.

8. The method of claim 1, wherein turpenes in the *cannabis* are collected in extracted water from step (c).

9. The method of claim 8, wherein the turpenes are selected from the group consisting of Hemiterpenes, Monoterpenes, Polyterpenes, Tetraterpenes, Terpenoid oxides, Sesterterpenes, Sesquiterpenes, Norisoprenoids and mixtures thereof.

* * * * *